(12) United States Patent
Naqvi et al.

(10) Patent No.: US 7,135,325 B2
(45) Date of Patent: Nov. 14, 2006

(54) SHORT ENZYME DONOR FRAGMENT

(75) Inventors: Tabassum Naqvi, Fremont, CA (US); Rajendra Singh, San Jose, CA (US); Riaz Rouhani, Concord, CA (US)

(73) Assignee: DiscoveRx, Inc., Fremont, CA (US)

( * ) Notice: Subject to any disclaimer, the term of this patent is extended or adjusted under 35 U.S.C. 154(b) by 0 days.

(21) Appl. No.: 10/422,262

(22) Filed: Apr. 24, 2003

(65) Prior Publication Data

US 2003/0219848 A1 Nov. 27, 2003

Related U.S. Application Data

(60) Provisional application No. 60/376,935, filed on May 2, 2002.

(51) Int. Cl.
*C12N 9/38* (2006.01)
*C12N 9/96* (2006.01)
*G01N 33/53* (2006.01)

(52) U.S. Cl. .................. 435/207; 435/288; 435/7.6; 530/300; 530/350; 530/387.1; 530/402

(58) Field of Classification Search .................. 435/207, 435/186, 7.6; 530/300, 350, 387.1, 402
See application file for complete search history.

(56) References Cited

U.S. PATENT DOCUMENTS 4,708,929 A * 11/1987 Henderson .................. 435/7.5
5,976,857 A * 11/1999 Powell et al. ............... 435/207

* cited by examiner

*Primary Examiner*—Tekchand Saidha
(74) *Attorney, Agent, or Firm*—Bertram Rowland; David J. Aston; Hana Verny

(57) ABSTRACT

Short enzyme donor fragments of β-galactosidase are provided of not more than 40 amino acids, where the short fragments are used as a label and may be substituted with a wide variety of organic compounds, particularly polypeptides having independent functional activity. The enzyme donor finds use in competitive and non-competitive assays, monitoring intracellular events, or other processes where a sensitive non-interfering label is desired.

12 Claims, 7 Drawing Sheets

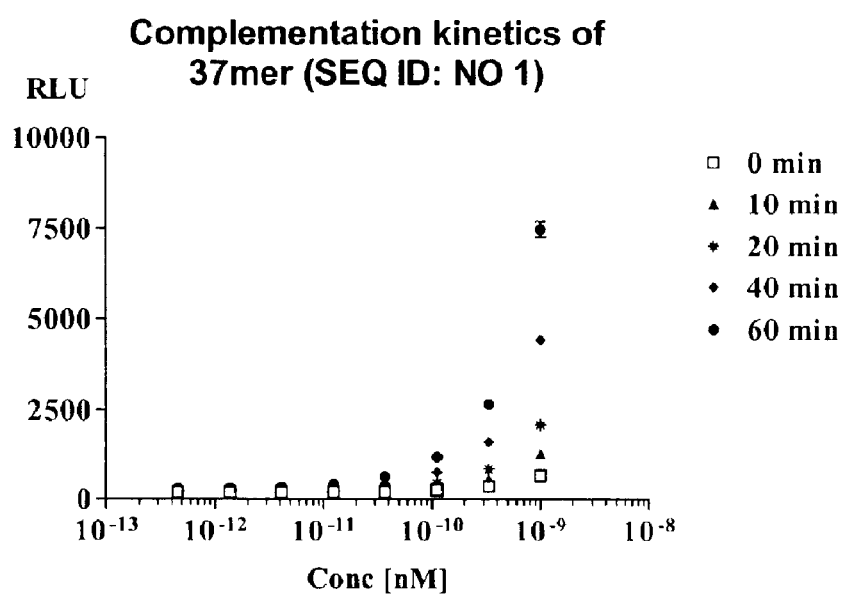
Fig. 1. Complementation kinetics of 37mer ED (SEQ ID NO 1) at different concentrations.

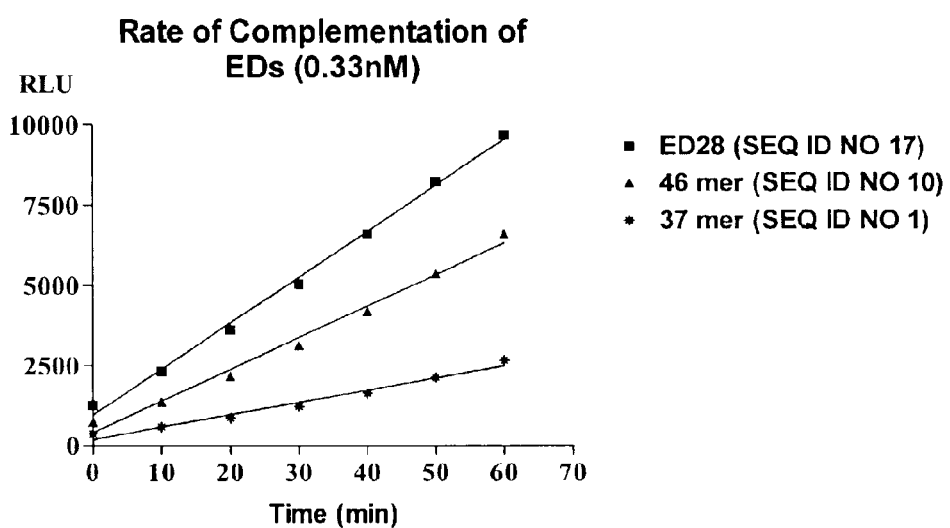
Fig. 2. Rate of complementation activities of 37mer ED (SEQ ID: NO 1), 46mer ED (SEQ ID: NO 10) and ED 28 (SEQ ID: NO 17) at a concentration of 0.33nM.

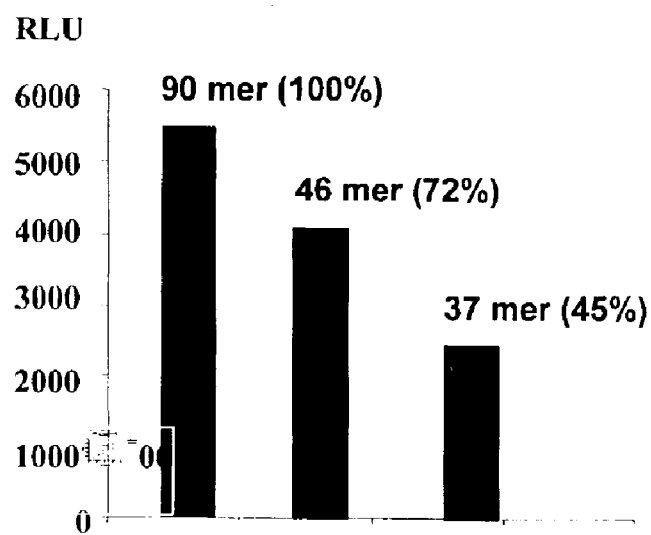
Fig. 3. Comparison of complementation activity of 37mer ED (SEQ ID: NO 1), 46mer ED (SEQ ID: NO 10) and ED 28 (SEQ ID NO 17) at concentration of 0.01nM.

| EDs | LLD (60 min) | Z' |
|---|---|---|
| ED28 | 0.16 pM | 0.8 |
| SEQ ID: NO 10 | 0.3 pM | 0.8 |
| SEQ ID: NO 1 | 1.0 pM | 0.5 |

Fig. 4. Lowest limit of detection of 37mer ED (SEQ ID NO 1), 46mer ED (SEQ ID: NO10) and ED 28 (SEQ ID NO 17).

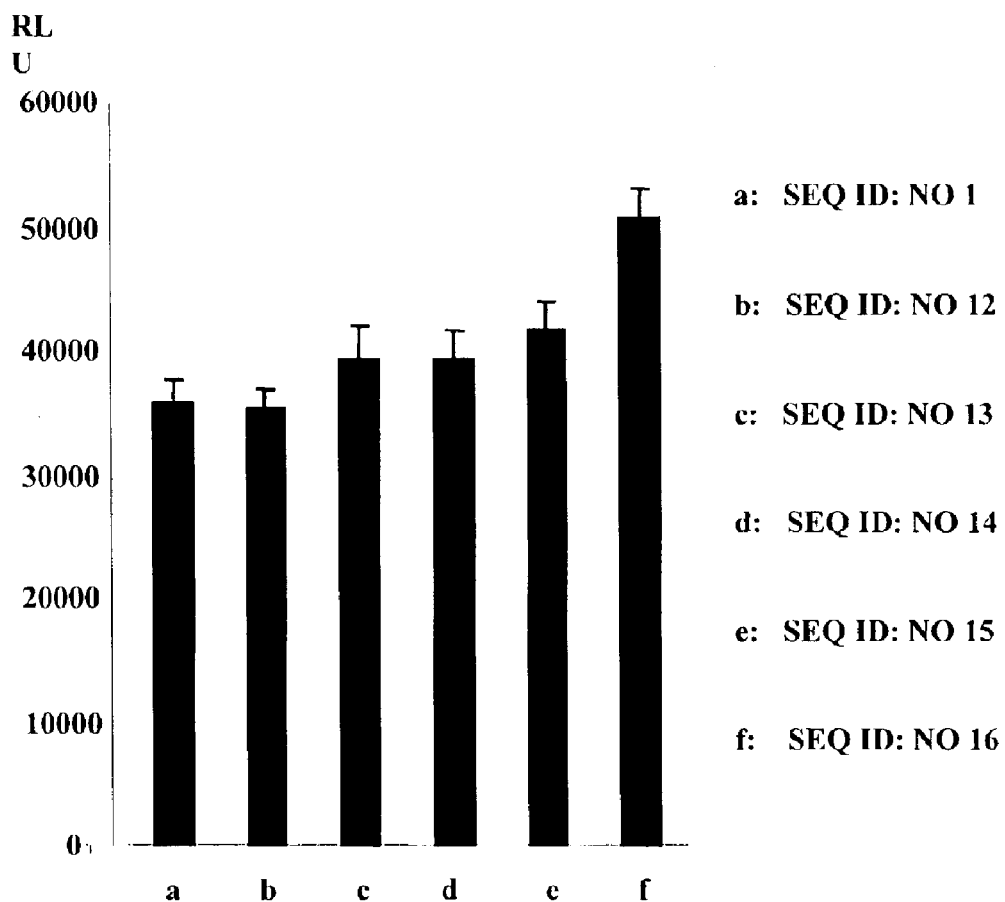
Fig. 5. Comparison of complementation activity of ED with different purification tags.

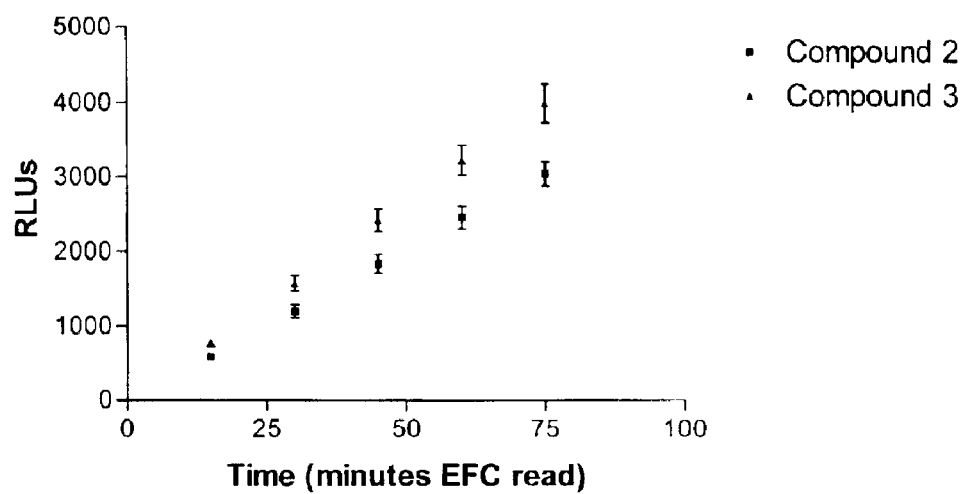
Fig. 6. Complementation kinetics of the 37mer ED (one Cys) oligonucleotide conjugates;

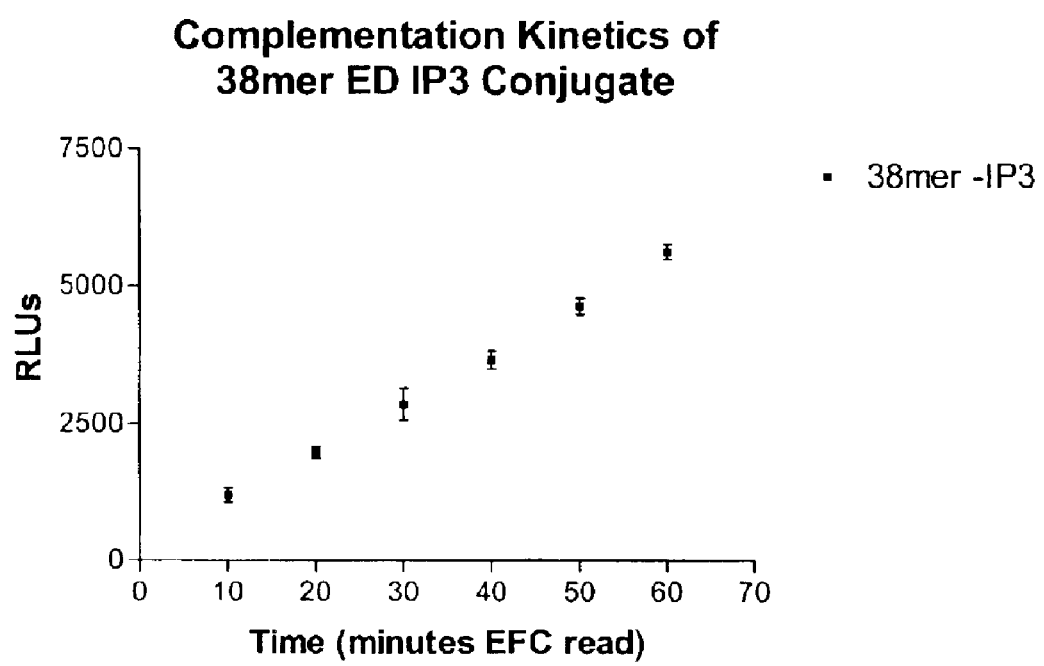
Fig. 7. Complementation kinetics of the 38mer ED (SEQ ID 20) $IP_3$ conjugate.

```
                          SEQUENCE LISTING

<160> NUMBER OF SEQ ID NOS: 22

<210> SEQ ID NO 1
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Leu Ala Val Val Leu Gln Arg Arg Asp Trp Glu Asn Pro Gly Val
 1               5                  10                  15

Thr Gln Leu Asn Arg Leu Ala Ala His Pro Pro Phe Ala Ser Trp Arg
            20                  25                  30

Asn Ser Glu Glu Ala
        35

<210> SEQ ID NO 2
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala His Pro Pro Phe Ala Ser Trp Arg Asn Ser Glu Glu Ala Arg Thr
 1               5                  10                  15

Asp Cys Pro Ser Gln Gln Leu
            20

<210> SEQ ID NO 3
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Thr Gln Leu Asn Lys Leu Ala Ala His Pro Pro Phe Ala Ser Trp
 1               5                  10                  15

Arg Asn Ser Glu Glu Ala Arg Thr Asp Cys Pro Ser Gln Gln Leu
            20                  25                  30

<210> SEQ ID NO 4
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Gln Arg Arg Asp Trp Glu Asn Pro Gly Val Thr Gln Leu Asn Arg
```

```
                 1               5                  10                 15
Leu Ala Ala His Pro Pro Phe Ala Ser Trp Arg Asn Ser Glu Glu Ala
                                20                 25                 30
Arg Thr Asp Cys Pro Ser Gln Gln Leu
            35                  40
```

<210> SEQ ID NO 5
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Ser Leu Ala Val Val Leu Gln Arg Arg Asp Trp Glu Asn Pro Gly Val
 1               5                  10                 15
Thr Gln Leu Asn Arg Leu Ala Ala His Pro Pro Phe
                20                  25
```

<210> SEQ ID NO 6
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Ala Ser Ser Asn Ser Leu Ala Val Val Leu Gln Arg Arg Asp Trp Glu
 1               5                  10                 15
Asn Pro Gly Val Thr Gln Leu Asn Arg Leu Ala Ala His Pro Pro Phe
                20                  25                 30
```

<210> SEQ ID NO 7
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Ile Asp Pro Cys Ala Ser Ser Asn Ser Leu Ala Val Val Leu Gln Arg
 1               5                  10                 15
Arg Asp Trp Glu Asn Pro Gly Val Thr Gln Leu Asn Arg Leu Ala Ala
                20                  25                 30
His Pro Pro Phe
            35
```

<210> SEQ ID NO 8
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

```
Ser Pro Gly Asn Ile Asp Pro Cys Ala Ser Ser Asn Ser Leu Ala Val
 1               5                  10                 15
Val Leu Gln Arg Arg Asp Trp Glu Asn Pro Gly Val Thr Gln Leu Asn
                20                  25                 30
```

-continued

Arg Leu Ala Ala His Pro Pro Phe
        35                  40

<210> SEQ ID NO 9
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Ser Ser Pro Gly Asn Ile Asp Pro Cys Ala Ser Ser Asn Ser Leu
1               5                   10                  15

Ala Val Val Leu Gln Arg Arg Asp Trp Glu Asn Pro Gly Val Thr Gln
            20                  25                  30

Leu Asn Arg Leu Ala Ala His Pro Pro Phe
        35                  40

<210> SEQ ID NO 10
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Leu Ala Val Val Leu Gln Arg Arg Asp Trp Glu Asn Pro Gly Val
1               5                   10                  15

Thr Gln Leu Asn Lys Leu Ala Ala His Pro Pro Phe Ala Ser Trp Arg
            20                  25                  30

Asn Ser Glu Glu Ala Arg Thr Asp Cys Pro Ser Gln Gln Leu
        35                  40                  45

<210> SEQ ID NO 11
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Ser Leu Ala Val Val Leu Gln Arg Arg Asp Trp Glu Asn Pro Gly
1               5                   10                  15

Val Thr Gln Leu Asn Lys Leu Ala Ala His Pro Pro Phe Ala Ser Trp
            20                  25                  30

Arg Asn Ser Glu Glu Ala Arg Thr Asp Cys Pro Ser Gln Gln Leu
        35                  40                  45

<210> SEQ ID NO 12
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Trp Arg His Pro Gln Phe Gly Gly Ser Leu Ala Val Val Leu Gln
1               5                   10                  15

Arg Arg Asp Trp Glu Asn Pro Gly Val Thr Gln Leu Asn Arg Leu Ala
            20                  25                  30

```
Ala His Pro Pro Phe Ala Ser Trp Arg Asn Ser Glu Glu Ala
         35                  40                  45
```

<210> SEQ ID NO 13
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

```
His His His His His His Ser Leu Ala Val Val Leu Gln Arg Arg Asp
 1               5                  10                  15

Trp Glu Asn Pro Gly Val Thr Gln Leu Asn Arg Leu Ala Ala His Pro
             20                  25                  30

Pro Phe Ala Ser Trp Arg Asn Ser Glu Glu Ala
         35                  40
```

<210> SEQ ID NO 14
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

```
Asp Tyr Lys Asp Asp Asp Tyr Lys Ser Leu Ala Val Val Leu Gln Arg
 1               5                  10                  15

Arg Asp Trp Glu Asn Pro Gly Val Thr Gln Leu Asn Arg Leu Ala Ala
             20                  25                  30

His Pro Pro Phe Ala Ser Trp Arg Asn Ser Glu Glu Ala
         35                  40                  45
```

<210> SEQ ID NO 15
<211> LENGTH: 49
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
His His His His His His Ser Leu Ala Val Val Leu Gln Arg Arg Asp
 1               5                  10                  15

Trp Glu Asn Pro Gly Val Thr Gln Leu Asn Arg Leu Ala Ala His Pro
             20                  25                  30

Pro Phe Ala Ser Trp Arg Asn Ser Glu Glu Ala Leu Val Pro Arg Gly
         35                  40                  45

Ser
```

<210> SEQ ID NO 16
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
His Asn His Asn His Asn His Asn His Asn His Asn Ser Leu Ala Val
 1               5                  10                  15
```

```
Val Leu Gln Arg Arg Asp Trp Glu Asn Pro Gly Val Thr Gln Leu Asn
            20                  25                  30

Arg Leu Ala Ala His Pro Pro Phe Ala Ser Trp Arg Asn Ser Glu Glu
        35                  40                  45

Ala Leu Val Pro Arg Gly Ser
    50                  55
```

<210> SEQ ID NO 17
<211> LENGTH: 90
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Met Asp Pro Ser Gly Asn Pro Tyr Gly Ile Asp Pro Thr Gln Ser Ser
 1               5                  10                  15

Pro Gly Asn Ile Asp Pro Cys Ala Ser Ser Asn Ser Leu Ala Val Val
            20                  25                  30

Leu Gln Arg Arg Asp Trp Glu Asn Pro Gly Val Thr Gln Leu Asn Arg
        35                  40                  45

Leu Ala Ala His Pro Pro Phe Ala Ser Trp Arg Asn Ser Glu Glu Ala
    50                  55                  60

Arg Thr Asp Cys Pro Ser Gln Gln Leu Ala Gln Pro Glu Trp Gly Leu
65                  70                  75                  80

Glu Ser Arg Ser Ala Gly Met Pro Leu Glu
                85                  90
```

<210> SEQ ID NO 18
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Ser Leu Ala Val Val Leu Gln Arg Arg Asp Trp Glu Asn Pro Gly Val
 1               5                  10                  15

Thr Gln Leu Asn Arg Leu Ala Ala His Pro Pro Phe Ala Ser Trp Arg
            20                  25                  30

Asn Ser Glu Cys Ala
        35
```

<210> SEQ ID NO 19
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Cys Ser Leu Ala Val Val Leu Gln Arg Arg Asp Trp Glu Asn Pro Gly
 1               5                  10                  15

Val Thr Gln Leu Asn Arg Leu Ala Ala His Pro Pro Phe Ala Ser Trp
            20                  25                  30

Arg Asn Ser Glu Cys Ala
        35
```

```
<210> SEQ ID NO 20
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gtctttctgc tc                                                              12

<210> SEQ ID NO 21
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtctttctgc tc                                                              12

<210> SEQ ID NO 22
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gtctttctgc tc                                                              12
```

SHORT ENZYME DONOR FRAGMENT

CROSS-REFERENCE TO RELATED APPLICATIONS

This application claims priority to provisional application Ser. No. 60/376,935, filed May 2, 2002, whose contents are specifically incorporated herein by reference.

BACKGROUND OF THE INVENTION

1. Field of the Invention

The invention relates to β-galactosidase fragment as a label.

2. Background Information

β-galactosidase has found wide use as a label in a variety of environments. Both the intact enzyme and fragments thereof have been used as a label in the determination of the presence of an analyte, interactions between different molecules, and the like. The enzyme is very versatile in having a high turnover rate, fluorescent, luminescent and light absorbent products from its catalyzed reactions, stable and active under a variety of conditions.

Because of its versatility, new applications are of great interest. In one application, one is interested in using the small fragment as a label fused to another protein. Such fusion products can find application in many situations, particularly intracellular situations, where one is interested in the fused protein accurately mimicking the activity of the natural protein. Desirably, the β-galactosidase fragment should be small, so as to provide the minimal interference with the activity, transport and interactions with other proteins. Heretofore, the small fragment has been greater than 40 amino acids, 43 amino acids having been identified as being active. Based on this disclosure it was not certain that one could further truncate the small fragment and obtain a complex with the large fragment that would have a sufficient turnover rate so as to be useful as a label.

The proteomics field is rapidly moving toward determining of the function of proteins, including their interaction, degradation and modulation. Consequently, a technology capable of measuring the function at low expression levels, particularly those levels at which proteins are expressed endogenously, is required for extensive deployment of functional proteomics in drug discovery. Enzyme fragment complementation (EFC) technology provides one such platform for addressing not only expression of proteins but also for deciphering protein-protein interactions. EFC is a generic term to describe the combination of enzyme fragments to form active enzyme, followed by detection of that activity by measurement of an hydrolysis product, generally by colorimetric, fluorometric or chemiluminescent methods. It has the advantage of providing an amplification step, due to enzyme turnover, as part of the detection system.

In one aspect of EFC, the fragments of the enzyme have sufficient affinity for each other to complex to form an active enzyme without relying on the affinity of the binding of complementary pairs to which the fragments are attached. This capability has been amply demonstrated with β-galactosidase, using a small enzyme donor (ED) fragment and a large enzyme acceptor (EA) fragment The enzyme donors that have been typically used in CEDIA® or EFC are typically 90 mers (amino acids), for example ED4, ED14 and ED28 are 90 mers with one cysteine, one cysteine plus one lysine and two cysteines respectively. These amino acids serve as handles for conjugating various molecules to the enzyme donor. The enzyme donors which are currently used in marketed CEDIA products are made by fermentation of genetically engineered bacteria, which need several processing steps culminating in a tedious purification of the product ED. This approach has worked for production purposes till now.

Advances made in peptide synthesis chemistry does enable 90 mers to be synthesized in useful amounts, however, the cost is still high when compared to the site directed mutagenisis approach of making ED variants. Shorter EDs (fewer than 50 mers) would make the synthetic EDs commercially competitive. Automated peptide synthesis is now routine in many laboratories, typically a 40–50 mer can be synthesized in a week. A disadvantage with the genetic approach to produce ED variants is that it is extremely time consuming and labor intensive and it takes the same amount of time to produce a 50 mer as a 90 mer which is in the vicinity of 6–8 weeks. From this perspective shorter synthetic EDs are attractive, first for research uses as variants can be synthesized with a turnaround time of a week (for 40 mers) and second the cost for scale up makes it competitive with the recombinant approaches for commercial use. The relative ease and flexibility with which shorter ED variants can be made by synthetic approaches makes it possible to study structure activity relationships to determine sequences that are essential for complementation activity. Since ED conjugates tend to alter complementation depending on the nature of the ligand that is appended, such structure activity relationships can be exploited to yield conjugates with improved performance.

RELEVANT LITERATURE

U.S. Pat. Nos. 4,378,428; 4,708,929; 5,037,735; 5,106,950; 5,362,625; 5,464,747; 5,604,091; 5,643,734; and PCT application nos. WO96/19732; and WO98/06648 describe assays using complementation of enzyme fragments. WO 00/039348, as indicated above, describes a protease assay where the marker is a β-galactosidase fragment fused to a protein having a specific protease cleavage site. There are numerous other references concerned with the use of β-galactosidase fragments in assay systems. The following are illustrative. Douglas, et al., Proc. Natl. Acad. Sci. USA 1984, 81:3983–7 describes the fusion protein of ATP-2 and lacZ. WO92/03559 describes a fusion protein employing α-complementation of β-galactosidase for measuring proteinases. WO01/0214 describes protein folding and/or solubility assessed by structural complementation using the α-peptide of β-galactosidase as a fusion protein. WO01/60840 describes fusion proteins including a fusion protein comprising an enzyme donor β-galactosidase for measuring protein folding and solubility. Homma, et al., Biochem. Biophys. Res. Commun., 1995, 215, 452–8 describes the effect of α-fragments of β-galactosidase on the stability of fusion proteins. Abbas-Terki, et al., Eur. J. Biochem. 1999, 266, 517–23 describes α-complemented β-galactosidase as an in vivo model susbtrate for the molecular chaperone heat-shock protein in yeast. Miller, et al., Gene, 1984, 29, 247–50 describe a quantitative β-galactosidase α-complementation assay for fusion proteins containing human insulin β-chain peptides. Thomas and Kunkel, Proc. Natl. Acad. Sci. USA, 1993, 90, 7744–8 describe an ED containing plasmid to measure mutation rate.

SUMMARY OF THE INVENTION

Polypeptides are provided that serve as enzyme donors to complex with a large fragment of β-galactosidase to form a functional enzyme. The shorter active polypeptides find advantages as labels, where protein constructs are prepared, in being more rapidly degraded and for intracellular determinations. The short oligopeptide may be joined to a variety of compounds of interest, particularly proteins, to determine the status of the compound, serving as a mimic of the natural compound. The short oligopeptide EDs may be used in a variety of assays and can be produced synthetically.

BRIEF DESCRIPTION OF THE DRAWINGS

FIG. 1 is a graph showing complementation kinetics of 37 mer ED (SEQ ID NO 1) at different concentrations.

FIG. 2 is a graph comparing the rate of complementation activities of 37 mer ED (SEQ ID NO 1), 46 mer ED (SEQ ID NO 10) and ED 28 (SEQ ID NO 17) at concentration of 0.33 nM.

FIG. 3 is a comparison of complementation activity of 37 mer ED (SEQ ID NO 1), 46 mer ED (SEQ ID NO 10) and ED 28 (SEQ ID NO 17) at concentration of 0.01 nM.

FIG. 4 shows the lowest limit of detection of 37 mer ED (SEQ ID NO 1), 46 mer ED (SEQ ID NO 10) and ED 28 (SEQ ID NO 17).

FIG. 5 is a comparison of complementation activity of ED with different purification tags.

FIG. 6 is a graph of the complementation kinetics of the 37 mer ED (one Cys) oligonucleotide conjugates;

FIG. 7 is a graph of the complementation kinetics of the 38 mer ED (SEQ ID 20) IP$_3$ conjugate.

DETAILED DESCRIPTION OF THE INVENTION

Novel oligopeptides are provided that serve as the enzyme donor fragment of a complex with the enzyme acceptor fragment of β-galactosidase. The oligopeptides are of not more than 40 amino acids of the β-galactosidase enzyme donor fragment and provide for improved properties and preparation due to their reduced size. The active sequence has substantially the natural sequence of the N-terminal proximal sequence of β-galactosidase, for the most part having the following amino acid sequence:

SLAVVLQRRDWENPGVTQLNRLAAHPP-FASWRNSEEA (SEQ ID NO: 1), and not more than a total of an additional 3 amino acids present at the termini, particularly of the natural β-galactosidase, and not more than 3 substitutions within the sequence, as the active ED by itself. For the most part, conservative substitutions are involved, where the non-polar aliphatic amino acids, such as G, A, V, L, and I may be substituted one for the other, the non-charged polar amino acids, such as C, M, S, T, N, and Q may be substituted one for the other, the charged amino acids may be substituted one for the other of the same charge, i.e. K and R; and D and E; and the aromatic amino acids may be substituted one for the other, F, W, and Y. For the most part, the active portion of the molecule will not be changed, except that it may be joined at either of its termini to a compound of interest, particularly a protein. The ED may be joined by an amino acid linker to a polypeptide of interest, generally of from about 1–10 amino acids, usually naturally occurring amino acids. The linker will ordinarily not be the natural sequence of the β-galactosidase that follows the 37–40 mer, so that the amino acid(s) following the active sequence will be other than the amino acid(s) that have found exemplification in the literature. Obviously, it is not a matter of operability, but rather the advantages of having as small an active ED as possible, so that the total molecular weight of the molecule is minimized.

While the subject sequence is derived from the β-galactosidase of *E. coli*, N-terminal proximal analogous sequences of β-galactosidase from other sources may also be used in a comparable manner. By analogous is intended that the sequence have at least 70% identity with the subject sequence in accordance with the BLAST program. The ED may be conjugated to any convenient moiety for performing various activities, such as assays, identification of specific moieties, hybridizing with nucleic acids, being linked to a cellular membrane, binding to lectins, etc. The ED may be joined to other than polypeptides, such as nucleic acids, sugars and lipids. Methods of conjugating such molecules to oligopeptides are well known in the literature and need not be expanded upon here. See, for example, U.S. patent application Nos. 2002/0197694, 2001/0007767, and references cited therein. In this way, various moieties may be identified by complexing with EA and performing the enzyme assay.

The ED is used with the EA to form an active β-galactosidase enzyme that can be detected by the addition of a detectable substrate, normally a colored, fluorescent or chemiluminescent substrate. β-galactosidase uses effectively fluorescers having phenolic groups that are etherified with a β-galactosyl group. The common substrates are β-D-galactopyranosyl phenols, such as fluorescein, mono- and di-susbtituted, o-nitrophenyl-β-D-galactoside, β-methylumbelliferyl-β-D-galactoside, X-gal, resorufin-β-D-galactoside, commercially available oxetanes, e.g. Galacto-Light Plus® kits (chemiluminescence) and chlorophenol red. The di-β-D-galactopyranosylfluorescein, and chlorophenol red-β-D-galactopyranoside may be used as intracellular markers.

The ED may be prepared by any convenient means. Where the ED is joined to other than a polypeptide, it may be synthesized by conventional means using commercially available synthesizers or it may be prepared using cloning, where the ED may be produced intracellularly and isolated by lysing or may be secreted, using an appropriate signal sequence. However, where a fusion protein is employed and the fusion protein substantially exceeds about 60 amino acids, usually cloning will be employed, where the protein may be isolated by lysis or from the medium by secretion as described above.

The ED may be joined to any compound of interest, where the ED will serve as a label. The ED may be joined to non-peptide compounds, namely organic compounds comprised of other than amino acids, where one is interested in such compounds binding to complementary binding member. Thus the EDs of the subject invention can be used in competitive and non-competitive assays for detecting the presence of drugs, antibodies, lectins, nucleic acids, sugars, or other analyte of interest. For examples of the use of EDs for the determination of analytes, see for example, U.S. Pat. Nos. 4,378,428; 4,708,929; 5,037,735; 5,106,950; 5,362,625; 5,464,747; 5,604,091; and 5,643,734, which are specifically incorporated by reference as illustrating the manner of performing the assays, where the EDs of the subject invention may be directly substituted for the EDs employed in the indicated references.

The EDs may be joined to various short sequences, where the sequence can provide for isolation, e.g. protease recognition sequences, for enzyme cleavage, for binding to a protein, etc. By having the short EDs, the EDs may be synthesized, so that any group can be attached to the ED during the synthesis. Where a short amino acid sequence is involved, then this sequence can be part of the synthesis. Where other than amino acids are involved, then an appropriately substituted amino acid can be used in the synthesis to include the substituent in the ED. Exemplary short amino acid sequences are streptavidin recognition sequence, caspase recognition sequence, thrombin recognition sequence, chelating sequences, such as polyhistidine or poly(histidine-arginine), etc.

The EDs of the subject invention find particular application in conjunction with polypeptides, e.g. oligopeptides and proteins, where the EDs, because of their smaller size are less likely to interfere with the function of the fused polypeptide, where degradation is of interest, will be rapidly degraded, and is less likely to adversely affect intracellular movements and interactions. As one illustration is WO 00/039348, which describes fusion proteins comprising an ED marker for determining solubility and folding of the fusion protein. By employing the substantially smaller EDs of the subject invention, the experience with the fusion protein is more likely to closely emulate the experience with the natural protein.

The fusion proteins of the subject invention find application both intra- and extracellularly, particularly the former. Where one is interested in degradation of the natural protein, the degradation of the fusion protein substantially eliminates background. For translocation, the smaller ED is less likely to interfere with the interaction of the natural protein with the other proteins involved with the translocation and, as applicable, crossing an organelle membrane.

For the preparation of the fusion protein and its expression construct, conventional splicing and insertion techniques are employed. The ED may be at the C-terminus, the N-terminus or both or internal to the fusion protein. Therefore, there may be one or more ED sequences in the fusion protein to enhance the number of ED units present per fusion protein to increase the observed signal with the fusion protein molecules present. The ED will come from the N-terminus of the β-galactosidase enzyme The fusion proteins will usually be selected to provide a functional protein that is soluble, does not aggregate so as to be unavailable for complexing, has substantially the natural folding, so as to be susceptible to binding to endogenous proteins that normally complex to the polypeptide fused to the ED, will be susceptible to the same proteases that such polypeptide is susceptible and will usually be able to perform substantially the same functions that such polypeptide performs. Therefore, the polypeptide is capable of acting as a surrogate for the natural protein to allow for measurements that are predictive of the activity of the natural protein.

The particular site of the ED in the fusion protein will depend upon the ability to include the ED in the coding sequence without significant reduction in the natural activity of the protein of interest. Thus, depending upon how much is known about the protein of interest, its structure, site(s) of binding to other entities, the folding pattern, as to loops, β-sheets and α-helices, the manner in which the ED activity will be modulated, e.g. degradation, steric interference of binding with EA by another entity, modification resulting in changes in conformation or charge, etc., the ED will be situated to provide the optimized response. For degradation, it will frequently not matter at what site the ED is situated, this is also likely to be true in many cases for steric interference, so long as the protein of interest retains its natural conformation and susceptibility to degradation and the ED retains its ability to activate the EA. However, for localized modification, such as phosphorylation or dephosphorylation, proteolytic cleavage for maturation, etc., usually it will be desirable to have the ED in proximity to the modified site. By knowing the structure of the protein, one can select loops, α-helices, β-sheets, sites of binding or the like to determine the site for insertion of the ED.

The ED may be inserted into the coding region in a variety of ways. For a cDNA gene, one may select a suitable restriction site for insertion of the sequence, where by using overhangs at the restriction site, the orientation is provided in the correct direction. Alternatively, one may use constructs that have homologous sequences with the target gene and allow for homologous recombination, where the homologous sequences that are adjacent in the target gene are separated by the ED in the construct. By using a plasmid in yeast having the cDNA gene, with or without an appropriate transcriptional and translational regulatory region, one may readily insert the ED construct into the cDNA gene at an appropriate site. Alternatively, one may insert the ED coding region with the appropriate splice sites in an intron or in an exon of the gene encoding the protein of interest. In this way, one can select for a site of introduction at any position in the protein. In some instances, it will be useful to make a number of constructs, where the ED is introduced into an intron and test the resulting proteins for ED activity and retention of function of the protein. Various other conventional ways for inserting encoding sequences into a gene can be employed. For expression constructs and decriptions of other conventional manipulative processes, See, e.g., Sambrook, Fritsch & Maniatis, "Molecular Cloning: A Laboratory Manual," Second Edition (1989) Cold Spring Harbor Laboratory Press, Cold Spring Harbor, N.Y. (herein "Sambrook et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins EDs. (1985)]; "Transcription And Translation" [B. D. Hames & S. J. Higgins, EDs. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

The fusion protein may have a protease recognition sequence, where the ED is released upon cleaving of the recognition sequence. The changes in the activity of the ED can be a result of the degradation of the fusion protein, by ubiquitination followed by degradation, protease degradation, denaturation, or other process. Alternatively, activity can be modified as a result of complex formation between the protein of interest and another protein. Activity can also be modified due to modification of the fusion protein, where the modification may result in complexing with another protein, change in the fusion protein conformation, presence of a substituent that changes the activity of the ED, or the like. Also, transport of the fusion protein to a compartment in the cell can result in a change in the measurable activity of the ED. In addition, where the modification affecting the ED activity is part of a pathway, the change in ED activity can be related to the events in the pathway. The fusion protein may comprise a protein of interest, a fragment of the protein of interest, a different polypeptide to represent the protein of interest or may be an intermediate for measuring some other protein or other activity.

Protein transport or translocation in the cell from the nucleus to another organelle or site, e.g. cytosol, cell membrane, proteasome, mitochondria, lysozome, Golgi, etc., can be of great importance to the biological properties of the protein and the cellular pathways of the cell. For protein transport, one can use leader sequences at the N terminus of the fusion protein from proteins that are known to be translocated to particular sites. One may also use coding sequences that result in modification of the fusion protein for binding the fusion protein to the cell membrane, such as sequences resulting in prenylation, myristoylation, farnesylation, etc. By providing for EA and substrate in the cell, depending upon the site of the fusion protein, one may be able to detect the presence of the fusion protein at the particular site. Alternatively, one may isolate organelles or part of the cell, e.g. microsomes, to determine the amount of the fusion protein associated with the cellular component.

In those cases where the ultimate goal is the production of a non-human transgenic animal, embryonic stem cells (ES cells) are preferred target cells. Such cells have been manipulated to introduce transgenes. ES cells are obtained from pre-implantation embryos cultured in vitro. Evans, M. J., et al. (1981), Nature, 292, 154–156; Bradley, M. O., et al. (1984), Nature, 309, 255–258; Gossler, et al. (1986), Proc. Natl. Acad. Sci. USA, 83, 9065–9069; and Robertson, et al. (1986), Nature, 322, 445–448. PNS vectors can be efficiently introduced into the ES cells by electroporation or microinjection or other transformation methods, preferably electroporation. Such transformed ES cells can thereafter be combined with blastocysts from a non-human animal. The ES cells thereafter colonize the embryo and can contribute to the germ line of the resulting chimeric animal. For review see Jaenisch, R. (1988), Science, 240, 1468–1474. In the present invention, PNS vectors are targeted to a specific portion of the ES cell genome and thereafter used to generate chimeric transgenic animals by standard techniques.

By having the native target protein as a fusion protein in its natural environment in a cell of interest, one can observe the natural effect of changes in the cell as a result of maturation, differentiation, changes in environment, and the like on the level of the protein in the cell. With embryonic stem cells, one can observe the variation in amount of the target protein over time as the cells undergo differentiation and migration to develop the foetus. The presence of the ED fused to a protein involved with foetal development, e.g. Hox proteins, morphogens, BMPs, homeobox proteins, etc., allows one to readily analyze for the expression of the proteins, the concentration level in the medium or intracellular, the changes in the concentration during development, the level of gradients of such proteins, and the like. Therefore, the ED can serve as an important research tool in elucidating the various mechanisms and pathways involved in the foetal development.

While the subject invention permits detection of events intracellularly, in some situations it will be necessary to lyse the cells and do the determination extracellularly. In this situation, either intact organelles or microsomes may be isolated, or the cell contents, particularly the cytoplasmic contents, isolated. The lysate may then be analyzed in accordance with conventional ways, adding EA, substrate and an appropriate buffer and measuring the signal.

Of the protein categories of interest, transcription factors, inhibitors, regulatory factors, enzymes, membrane proteins, structural proteins, and proteins complexing with any of these proteins, are of interest. Specific proteins include enzymes, such as the hydrolases exemplified by amide cleaving peptidases, such as caspases, thrombin, plasminogen, tissue plasminogen activator, cathepsins, dipeptidyl peptidases, prostate specific antigen, elastase, collagenase, exopeptidases, endopeptidases, aminopeptidase, metalloproteinases, including both the serine/threonine proteases and the tyrosine proteases,; hydrolases such as acetylcholinesterase, saccharidases, lipases, acylases, ATP cyclohydrolase, cerebrosidases, ATPase, sphingomyelinases, phosphatases, phosphodiesterases, nucleases, both endo- and exonucleases,; oxidoreductases, such as the cytochrome proteins, the dehydrogenases, such as NAD dependent dehydrogenases, xanthine dehyrogenase, dihydroorotate dehydrogenase, aldehyde and alcohol dehydrogenase, aromatase,; the reductases, such as aldose reductase, HMG-CoA reductase, trypanothione reductase, etc., and other oxidoreductases, such as peroxidases, such as myeloperoxidase, glutathione peroxidase, etc., oxidases, such as monoamine oxidase, myeloperoxidases, and other enzymes within the class, such as NO synthase, thioredoxin reductase, dopamine β-hydroxylase, superoxide dismutase, nox-1 oxygenase, etc.; and other enzymes of other classes, such as the transaminase, GABA transaminase, the synthases, β-ketoacyl carrier protein synthase, thymidylate synthase, synthatases, such as the amino acid tRNA synthatase, transferases, such as enol-pyruvyl transferase, glycinamide ribonucleotide transformylase, COX-1 and -2, adenosine deaminase.

Kinases are of great significance, such as tyrosine kinases, the MAP kinases, the cyclin dependent kinases, GTP kinases, ser/thr kinases, Chk1 and 2, etc.

Also of interest are enzyme inhibitors, such as $\alpha_1$-antitrypsin, antithrombin, cyclophilin inhibitors, proteasome inhibitors, etc.

Neuronal proteins, such as β-amyloid, TNF, prion, APP, transporters, e.g. dopamine transporter, receptors, such as NMDA receptors, AMDA receptors, dopamine receptors, channels, etc.

Another class of proteins is the transcription factors and their inhibitors or regulatory proteins, such as Adr Ace, Amt, AP, Atf, Att, Baf, Brn, Btf, C Ebp, C Jun, C Ets, CREB, CF, Chop, DP, E2F, Elk, Gata, Hnf, Iii A-H, Irf, NY Y, Otf, NFκB, NF-AT, Oct-1, Pea, Pit, PU, S, SP, Stat, Tef, TFIII, TFIIII, Ubf and Usf, while the inhibitors include Erk, IκB, LIF, Smad, RANTES, Tdg, etc., as well as other proteins associated with pathways that induce transcription factor synthesis, activation or inhibition.

In some instances, housekeeping proteins will be of interest, such as the proteins involved in the tricarboxylic acid cycle, the Krebs cycle, glycogenesis, etc.

As indicated previously, the genes of each of these proteins may be manipulated in numerous ways to fuse ED with the protein while maintaining the biological activity of the protein and ED.

Other proteins of interest are the oncogenes, such as Src, Ras, Neu, Erb, Fos, Kit, Jun, Myc, Myb, Abl, Bcl, etc. Cytokines, such as the interferons, α-γ, interleukins, 1–19, and integrins, adhesins, TNF, receptors, hormones, colony stimulating factors, growth factors, such as epidermal growth factor, fibroblast growth factor, etc., bone morphogenetic proteins, developmental proteins, such as the Hox proteins, or other proteins binding to or regulating proteins binding to homeoboxes, e.g. the hedgehog proteins, basement membrane proteins, heat shock proteins, proteins containing Krupple and Kringle structures chaperonins, calcium associated proteins, e.g. calmodulin, calcineurin, etc., membrane channels, transporter proteins, etc.

Also of interest are the proteins associated with proliferation, such as the cyclins, cyclin dependent kinases, p53, RB, etc.

For each of the applications using the EDs of the subject invention, kits can be provided having a source of EA, either as the protein or an expression construct for cellular introduction, a source of ED, as itself or as a fusion protein, again as the protein itself or as an expression construct for cellular introduction, a conjugate with other than a polypeptide, one or more substrates, buffer, and other reagents.

As indicated previously, the genes of each of these proteins may be manipulated in numerous ways to fuse ED with the protein while maintaining the biological activity of the protein and ED.

The following examples are intended to illustrate but not limit the invention.

Experimental

Materials and Methods

All Fmoc-protected amino acids were bought from Nova biochem, San Diego, Calif. The first amino acid loaded-PEG-resin and the Kaiser test reagents were bought from, Applied Biosystems, Foster city, Calif. All other reagents were from Fisher Scientific and Sigma Chemicals, St Louis.

Synthesis of ED Fragment

All the short ED fragments of β-galactosidase were synthesized using solid phase peptide chemistry either manually or on an automated peptide synthesizer employing Fmoc chemistry under $N_2$ stirring. The maual synthesis was carried out using low loaded PEG-Resin (loading 0.1–0.2 mmole/g resin) using appropriately loaded first Fmoc-amino acid residues. The couplings were performed using 4 equivalents of Fmoc-protected amino acids, 4 equivalents of benzotriazole-1-yl-oxy-tris-pyrrolidino-phosphonium hexafluorophosphate (PyBop), 4 equivalents of 1,Hydroxybenzotriazole (HOBt) and 8 equivalents of Diisopropylethylamine (DIPEA) reagent. The deprotection of the Fmoc group was carried out employing 20% piperidine in DMF. All couplings and deprotections were carried out in DMF. The couplings were monitored by Kaiser test at 100° C. In the case of secondary amino acids the efficiency of the coupling was monitored by chloranil test. The difficult peptide couplings were carried out for prolonged period of time in 0.1% TritonX-100 in DMF. After every 10 mer- an aliquot of the resin was taken out, deprotected using neat Trifluoroacetic acid (TFA) containing a cocktail of scavengers, purified by RP-HPLC (C18, 300 A°) and the molecular weight corroborated by ESIMS/MALDI-MS. The final peptide was obtained by treating the peptide resin with neat TFA containing thioanisole, ethanedithiol, water and phenol for 5 hours at ambient temperature. The resin was filtered off and the filtrate concentrated in vacuo. Addition of anhydrous cold ether yielded the crude peptide as a white powder. The product was finally purified under reverse phase conditions on a C18 column and the molecular weight corroborated by ESIMS.

EA and ED Complementation Assays

The complementation kinetics for all the ED fragments was carried out in a multiwell plate. Serial dilutions of different enzyme fragments (starting range 1 nM) with 1×EA reagent for complementation were employed. The assay protocol was as follows: To 20 ul of assay buffer, 10 ul of ED (serial dilutions in ED dilution buffer) and 1×EA reagent were added. After two hours of incubation at room temperature 10 ul of fluorescence or chemiluminescence reagent was added. The plate was read using a Packard plate reader at 10 min time intervals for 2 h. With resorufin galactoside (Molecular Probes, Eugene, Oreg.) as the fluorescence substrate an excitation wavelength of 530 mn and emission wavelength of 610 nm were used with PMT set at 1100V. The assay was performed in quadruplets.

| | | |
|---|---|---|
| 1. AHPPFASWRNSEEARTDCPSQQL (23 mer) | | (SEQ ID NO: 2) |
| 2. VTQLNKLAAHPPFASWRNSEEARTDCPSQQL (31 mer) | | (SEQ ID NO: 3) |
| 3. LQRRDWENPGVTQLNRLAAHPPFASWRNSEEARTDCPSQQL (41 mer) | | (SEQ ID NO: 4) |
| 4. SLAVVLQRRDWENPGVTQLNRLAAHPPF (28 mer) | | (SEQ ID NO: 5) |
| 5. ASSNSLAVVLQRRDWENPGVTQLNRLAAHPPF (32 mer) | | (SEQ ID NO: 6) |
| 6. IDPCASSNSLAVVLQRRDWENPGVTQLNRLAAHPPF (36 mer) | | (SEQ ID NO: 7) |
| 7. SPGNIDPCASSNSLAVVLQRRDWENPGVTQLNRLAAHPPF (40 mer) | | (SEQ ID NO: 8) |
| 8. QSSPGNIDPCASSNSLAVVLQRRDWENPGVTQLNRLAAHPPF (42 mer) | | (SEQ ID NO: 9) |
| 9. SLAVVLQRRDWENPGVTQLNRLAAHPPFASWRNSEEA (37 mer) | | (SEQ ID NO: 1) |
|    SLAVVLQRRDWENPGVTQLNKLAAHPPFASWRNSEEARTDCPSQQL (46 mer) | | (SEQ ID NO: 10) |
| 11. CSLAVVLQRRDWENPGVTQLNKLAAHPPFASWRNSEEARTDCPSQQL (47 mer) | | (SEQ ID NO: 11) |
|    Enzyme fragment with purification and cleavage TAGS | | |
| 12. AWRHPQFGGSLAVVLQRRDWENPGVTQLNRLAAHPPFASWRNSEEA (Strep Tag in 37 mer) | | (SEQ ID NO: 12) |
| 13. HHHHHHSLAVVLQRRDWENPGVTQLNRLAAHPPFASWRNSEEA (6His Tag in 37 mer) | | (SEQ ID NO: 13) |
| 14. DYKDDDYKSLAVVLQRRDWENPGVTQLNRLAAHPPFASWRNSEEA (Flag Tag in 37 mer) | | (SEQ ID NO: 14) |
| 15. HHHHHHSLAVVLQRRDWENPGVTQLNRLAAHPPFASWRNSEEALVPRGS | | (SEQ ID NO: 15) |
|    (6His Tag in 37 mer with Thrombin cleavage site at C-terminal) | | |
| 16. HNHNHNHNHNHNSLAVVLQRRDWENPGVTQLNRLAAHPPFASWRNSEEALVPRGS | | (SEQ ID NO: 16) |
|    {6(His-Asn) Tag in 37 mer with thrombin cleavage site at C-terminal) | | |
| 17. ED28 | | |
|    MDPSGNPYGIDPTQSSPGNIDPCASSNSLAVVLQRRDWENPGVTQLNRLAAHPPFASWRNS | | (SEQ ID NO: 17) |
|    EEARTDCPSQQLAQPEWGLESRSAGMPLE (90 mer) | | |
| 18. ED[36 + Cys]-BMH-5'-GTC TTT CTG CTC-3']:Compound 2 | | (SEQ ID NOS 20, 21 or 22) |

(SEQ ID NO: 18)
Ac-NH-SLAVVLQRRDWENPGVTQLNRLAAHPPFASWRNSECA

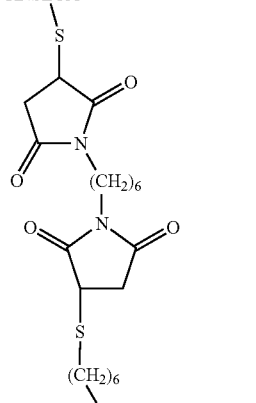

GTC TTT CTG CTC
(SEQ ID NOS 20, 21 or 22)

19. [5'-GTC TTT CTG CTC-3']-BMH-ED[36 + Cys]:Compound 3 (SEQ ID NOS 20, 21 or 22)

(SEQ ID NO: 18)
Ac-NH-SLAVVLQRRDWENPGVTQLNRLAAHPPFASWRNSECA

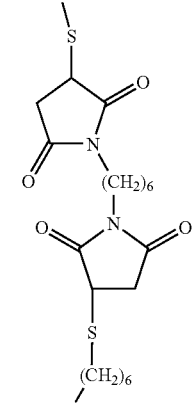

GTC TTT CTG CTC
(SEQ ID NOS 20, 21 or 22)

20. CSLAVVLQRRDWENPGVTQLNRLAAHPPFASWRNSECA 38mer (36 + 2Cys), (SEQ ID NO: 19)

Results
1. The SAR studies of the native 90 mer (ED 28) SEQ ID 17, demonstrated that 37 mer SEQ ID 1, retained 45% of the complementation activity at ED concentration of 0.0123 nM at 60 min. The rate of complementation was linear.
2. The complementation activity of the previous 46 mer SEQ ID 10, was 72% at the same concentration
3. Addition of different purification tags as well as thrombin cleavage site to (37 mer) improved the complementation kinetics 5–10%.
4. The other short EnzymeDonor fragments retained 3–6% activity of the native 90 mer (SEQ ID: NO 17)
5. The lowest limit of detection for SEQ ID:NO 1 was in sub picomolar range indicating that it retained its sensitivity when compared to native 90 mer (SEQ ID:NO 17)

The following is the preparation of IP3 derivatives having 36 amino acids from β-galactosidase and from 1–2 cysteines for conjugation to ligand.

Preparation of the D-myo-inositol-1-(3-(3-maleimidopropionyl) aminopropyloxy)-4,5-triphosphate.

To a solution of D-myo-inositol-1-(3-aminopropyloxyphosphato)-4,5-diphosphate (1 mg) in sodium phosphate (100 mM, pH 8.0, 1 mL) was added 200 μL of dry acetonitrile. Succinimidyl 3-maleimidopropionate (3 mg) was dissolved in minimum of acetonitrile (~200 μL). The maleimide solution was slowly added to the amine solution and mixed by vortexing. The product was purified by high performance liquid chromatography on a reversed phase column (C18).

Preparation of the Conjugate of 38 mer ED (36 mer Plus Two Cysteines) with D-myo-inositol-1-(3-(3-maleimidopropionyl) aminopropyloxy)-4,5-triphosphate (38 mer ED-(1P)mp-1,4,5-IP3).(with cysteine as the first amino acid of the 37 mer)(Compound 1)

38 mer ED (0.3 mg) was conjugated to D-myo-inositol-1-(3-(3-maleimidopropionyl)aminopropyloxy)-4,5-triphosphate (0.25 mg) in water (pH adjusted to 7.0 by adding 2 M ammonium acetate solution. After one hour the product was purified by high performance liquid chromatography on a reversed phase column (C18). The identity of the product was confirmed by MALDI-TOF analysis (M+=5592).

Preparation of the 37 mer ED (36 mer Plus One Cysteine):

37 mer ED (36 mer plus one cysteine) was synthesized by automated peptide synthesis using 0.1 mmole F-moc chemistry on an ABI 433A peptide synthesizer (Applied Biosystems, Foster City, Calif.). The final peptide was deprotected, N-acetylated and cleaved off the resin using trifluoroacetic acid containing a cocktail of scavengers (thioanisole, ethanedithiol and phenol). The deprotected peptide was purified by high performance liquid chromatography on a reversed phase column (C18).

Preparation of 37 mer ED[36 mer Plus One Cysteine] Conjugate to 1,6-bismaleimidohexane (ED[36+Cys]-BMH):

A solution of 37 mer ED[36+Cys] in sodium phosphate buffer (pH 7.0, 100 mM, 1 mL) was added to a solution of BMH (0.5 mg, Pierce, Rockford, Ill.) in dimethylformamide (1 mL) with mixing by rigorous vortex action. After complete addition the reaction mixture was allowed to stand at room temperature for 60 min. The product was purified by high performance liquid chromatography on a reversed phase column (C18). Analysis of the product by electrospray ionization mass spectroscopy confirmed the identity of the product (M+=4509).

Thiol-modified at 3' and 5' ends were prepared by Integrated DNA Technologies (Coralville, Iowa). The sequences are as follows:

TABLE 2

Sample EOS Signaling Network Management Processing Rules

| SNM Category | SNM Message Type | Action When Received | Generating Entity |
|---|---|---|---|
| CHM | COO<br>COA<br>X_COO<br>X_COA<br>CBD<br>CBA | Processed as for TPC. Not forwarded to remote application. | Generated by EOS on behalf of remote application. |
| DLM | DLC<br>CSS<br>CNS<br>CNP | Processed as for TPC. Not forwarded to remote application. | Generated by EOS on behalf of remote application. |
| ECM | ECO<br>ECA | Processed as for TPC. Not forwarded to remote application. | Generated by EOS on behalf of remote application. |
| FCM | RCT | The EOS abates congestion on behalf of the remote application.<br>Processed as for TPC. Not forwarded to remote application. | Generated by EOS on behalf of remote application.<br>A remote application can generate using MTPP, but this behavior is not recommended, since this results in excessive RCTs (sent by both EOS and remote application). |
|  | TFC | The EOS abates congestion on behalf of the remote application.<br>Processed as for TPC. Replicated to remote application using MTPP. | Generated by EOS on behalf of remote application. |
| MIM | LIN<br>LUN<br>LIA<br>LUA<br>LID<br>LFU | Processed as for TPC. Not forwarded to remote application. | Generated by EOS on behalf of remote application. |

TABLE 2-continued

Sample EOS Signaling Network Management Processing Rules

| SNM Category | SNM Message Type | Action When Received | Generating Entity |
|---|---|---|---|
|  | LLI<br>LRI |  |  |
| RSM | RSP<br>RSR<br>RCP<br>RCR | Processed as for TPC. Not forwarded to remote application. | Generated by EOS on behalf of remote application. |
| TFM | TFP<br>TCP<br>TFA<br>TCA | Processed as for TPC and replicated to remote application using MTP Primitive (MTPP). | If concerning remote application, then generated internally by EOS on behalf of remote application, but not transmitted.<br>If not concerning remote application, then generated and transmitted as usual. |
|  | TFR<br>TCR | Processed as for TPC. Not forwarded to remote application. | May be generated by EOS, but never on behalf of a remote application. |
| TRM | TRA<br>TRW | Processed as for TPC. Not forwarded to remote application. | Generated by EOS on behalf of remote application. |
| UFC | UPU | Forwarded to remote application if concerned SI is assigned, otherwise processed as for TPC. | May be generated by EOS or by remote application. |

Conjugation of the [5'-/HS—(CH$_2$)$_6$-GTC TTT CTG CTC-3']([SEQ ID NO: 20) to ED[36+1]-BMH" (ED[36+1]-BMH-[5'-GTC TTT CTG CTC-3'])([SEQ ID NO: 22)

Oligonucleotide was treated with dithiothreitol and purified by high performance liquid chromatography on a reversed phase column (C18) prior to conjugation to ED36+1-BMH. To a solution of ED[36+1]-BMH in HPLC water was added purified deprotected oligonucleotide [5'-/HS—(CH$_2$)$_6$/GTC TTT CTC-3'](SEQ ID NO: 20). The reaction was allowed to proceed for 60 minutes. The conjugate was purified by high performance liquid chromatography on a reversed phase column (C18). Analysis of the product by MALDI-TOF gave the expected molecular weight (M=8274).

Complementation Kinetics of 37 mer ED Oligonucleotides and 38 mer ED-IP3 Conjugates A 1.0 nM solution of the conjugate was prepared in enzyme dilution buffer (EDDB pH 5.5, 10 mM MES, 200 mM NaCl, 10 mM EGTA, 2 mg/mL BSA fragments and 14.6 mM NaN$_3$). The assay was performed by incubating 10 µl of the 1 nM solution with 10 µl of enzyme acceptor buffer (EADB pH 6.9, 100 mM PIPES, 400 mM NaCl, 10 mM EGTA, 0.005% Tween, 10 mM Mg(OAc)$_2$ and 14.6 mM NaN$_3$) and 10 µl of the enzyme acceptor (EA, 3.6 µM) for 30 minutes in a 384 well Costar plate (Corning Incorporated, NY). 10 µl of the Chemiluminescent substrate (Galacton Star with Emerald Plus from Applied Biosystems, Foster City, Calif.) was added to the mixture in the well and the plate read in a microplate luminometer (Lumicount, Packard BioScience, Meriden, Conn.). The read settings were 1100 volts on the PMT with a gain of 1.0 and an integration of 1.0 second. Readings were accumulated at 10–15 minute intervals. See FIGS. 6 and 7.

It is evident from the above results that a short ED can provide desired levels of sensitivity for use in assays, for the determination of analytes, for following events intracellularly, and the like. By being short enough to be readily synthesized, flexibility is provided for having both polypeptide and non-amino acid substitutions. In this way, one can study a variety of reactions resulting in cleavage, degradation, complex formation, translocation, and the like, where the short ED diminishes the likelihood of interference with these processes, while providing sufficient sensitivity for monitoring these events.

Although the invention has been described with reference to the above examples, it will be understood that modifications and variations are encompassed within the spirit and scope of the invention. Accordingly, the invention is limited only by the following claims.

What is claimed is:

1. In a cell, an enzyme donor for complementation with an enzyme acceptor fragment of E. coli β-galactosidase, said enzyme donor having from 37 to 40 amino acids of the N-terminal proximal β-galactosidase sequence as a fusion protein linked to a polypeptide of interest.

2. An enzyme donor according to claim 1, wherein said amino acids have the sequence SEQ ID:NO 1, with not more than a total of three additional amino acids at the termini.

3. An enzyme donor according to claim 2 where the fragment of β-galactosidase is SEQ ID:NO 1.

4. An enzyme donor for complementation with an enzyme acceptor fragment of E. coli β-galactosidase having from 37 to 40 amino acids of the N-terminal proximal β-galactosidase sequence joined by an amino acid linker of from about 1–10 amino acids to a polypeptide of other than the succeeding naturally occurring β-galactosidase sequence of said enzyme donor.

5. An enzyme donor according to claim 4, wherein said amino acids have the sequence SEQ ID:NO 1, with not more than a total of three additional amino acids at the termini.

6. An enzyme donor according to claim 5, where the fragment of β-galactosidase is SEQ ID:NO 1.

7. A method for performing an assay intracellularly using enzyme fragment complementation employing a fusion protein comprising a fragments of an E. coli β-galactosidase having from 37 to 40 amino acids of the N-terminal proximal β-galactosidase sequence joined to a polypeptide of interest, wherein the cells employed express said fusion protein, said method comprising:

expressing said fusion protein in said cells; and determining the presence of said fusion protein by contacting said fusion protein with an enzyme acceptor and a fluorescent or chemiluminescent β-galactosidase substrate.

8. A method according to claim 7, wherein said enzyme donor is joined to a functional polypeptide expressed in said cells and other than the succeeding naturally occurring β-galactosidase sequence of said enzyme donor.

9. A method according to claim 7, wherein said enzyme donor is joined to a protease recognition sequence.

10. A method according to claim 8, wherein said enzyme donor is joined to an enzyme.

11. A method according to claim 8, wherein said enzyme donor is joined to a polypeptide in the pathway regulating transcription.

12. A kit comprising a cell according to claim 1.

* * * * *

UNITED STATES PATENT AND TRADEMARK OFFICE
CERTIFICATE OF CORRECTION

| | | |
|---|---|---|
| PATENT NO. | : 7,135,325 B2 | Page 1 of 2 |
| APPLICATION NO. | : 10/422262 | |
| DATED | : November 14, 2006 | |
| INVENTOR(S) | : Tabassum Naqvi et al. | |

It is certified that error appears in the above-identified patent and that said Letters Patent is hereby corrected as shown below:

Sheet 3 of 7, FIG. 3.

Remove the "0)" next to the first bar graph on the histogram.

Delete drawing sheet 3 of 7 and substitute therefor the attached drawing sheet containing figure 3.

Column 12,

Line 4, delete "dry" after the word "of" and before the word "acetonitrile".

Signed and Sealed this

Nineteenth Day of February, 2008

JON W. DUDAS
*Director of the United States Patent and Trademark Office*

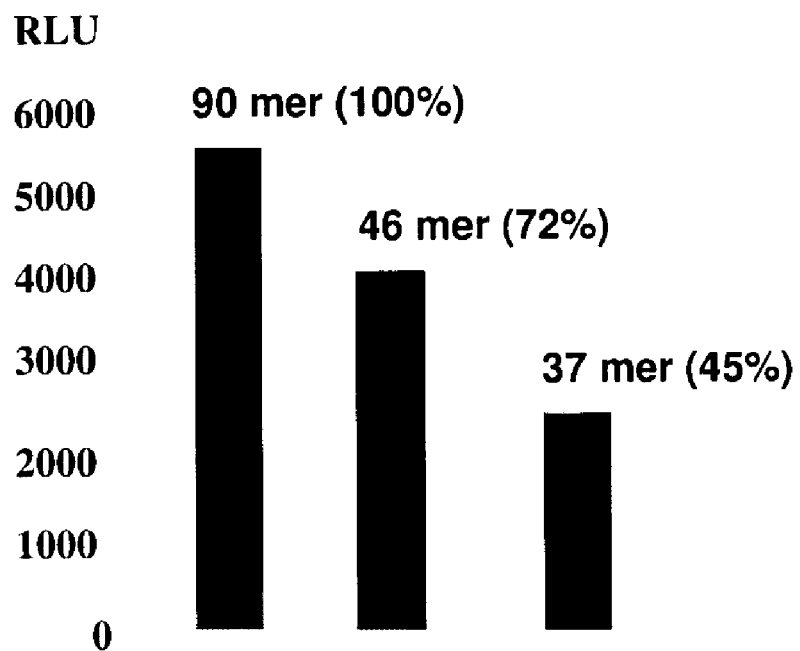
Fig. 3. Comparison of complementation activity of 37mer ED (SEQ ID NO: 1), 46mer ED (SEQ ID: NO 10) and ED 28 (SEQ ID NO 17) at concentration of 0.01 nM.